United States Patent [19]

Boursier

[11] Patent Number: 4,840,797
[45] Date of Patent: Jun. 20, 1989

[54] CONFECTIONERY OR PHARMACEUTICAL PRODUCT WITH A SUGARLESS COATING OBTAINED BY HARD COATING AND METHOD FOR ITS PREPARATION

[75] Inventor: Bernard Boursier, Violaines, France

[73] Assignee: Roquette Freres, Lestrem, France

[21] Appl. No.: 854,135

[22] Filed: Apr. 21, 1986

[30] Foreign Application Priority Data

Apr. 30, 1985 [FR] France .................. 85 06579

[51] Int. Cl.$^4$ .................. A23G 3/30; A23G 7/00; A01N 25/00
[52] U.S. Cl. .................. 424/475; 426/103; 426/302; 426/5
[58] Field of Search .................. 426/103, 302, 660; 424/35, 440

[56] References Cited

U.S. PATENT DOCUMENTS

| | | |
|---|---|---|
| 3,918,986 | 11/1975 | Hiraiwa .................. 426/103 |
| 4,238,510 | 12/1980 | Cherukuri et al. . |
| 4,293,570 | 10/1981 | Vadasz . |
| 4,357,314 | 11/1982 | Lynch . |
| 4,381,318 | 4/1983 | Lynch . |
| 4,423,086 | 12/1983 | Devos et al. .................. 427/3 |
| 4,457,921 | 7/1984 | Stroz et al. .................. 424/49 |
| 4,497,846 | 2/1985 | Boursier et al. .................. 426/660 |

FOREIGN PATENT DOCUMENTS

| | | |
|---|---|---|
| 2467597 | 10/1979 | France . |
| 2486364 | 7/1980 | France . |
| 2522250 | 3/1982 | France . |

OTHER PUBLICATIONS

Chem. Abstracts vol. 82, 171360q.

Primary Examiner—Joseph L. Schofer
Assistant Examiner—Peter F. Kulkosky
Attorney, Agent, or Firm—Larson and Taylor

[57] ABSTRACT

Confectionery or pharmaceutical product with the sugarless coating obtained by hard coating, this coating being essentially crystalline and comprising at least 90% by weight of maltitol.

8 Claims, No Drawings

CONFECTIONERY OR PHARMACEUTICAL PRODUCT WITH A SUGARLESS COATING OBTAINED BY HARD COATING AND METHOD FOR ITS PREPARATION

The invention relates to a confectionery or pharmaceutical product with a sugarless coating obtained by hard coating.

It is aimed also at the process of preparing this product.

So-called "hard coating" is distinguished from so-called "soft coating" in the sense that the constituent material of the coating is crystalline, the water contained in said material being evaporated.

Confectionery products, that is to say chewing-gums, chewing pastes, bonbons and licorices, and pharmaceutical products in the form of tablets, pills or bonbons with a sugarless coating obtained by a hard coating, are already known.

In these products, the surgarless coating obtained by hard coating is based on xylitol and, in a lesser extent, on mannitol.

More recently, a hard coating method, enabling, against all expectation, production of a hard coating based on sorbitol, has been developed.

This method and the resulting product give entire satisfaction but, by reason the constantly growing needs of the pharmaceutical and confectionery industries for products with a sugarless hard coating, Applicant has continued its research and had the merit of finding that it was possible to produce a coating of the type concerned based on maltitol.

Consequently, the confectionery or pharmaceutical product having a sugarless hard coating according to the invention, is characterized by the fact that said coating is essentially crystalline and comprises at least 90% by weight of maltitol.

And the method of preparing the abovesaid product is characterized by the fact that there is applied a maltitol syrup
—of maltitol richness higher than 92%, preferably than 95% by weight to dry matter, and more preferably higher than 96%,
—of dry matter content from 50 to 70% by weight, preferably from 55 to 65% by weight and
—of temperature less than 70° C. and, preferably, from 45° to 65° C.,
on a moving bed of cores to be coated, the temperature existing in said moving core bed being less than 55° C. and preferably from 20° to 40° C., all of the abovesaid conditions being selected, within the above-mentioned ranges, so that, when the maltitol syrup arrives in contact with the cores to be coated, that is to say at the temperature existing within the moving core bed, it is at a saturation level of 0.70 to 0.90 and, preferably, from 0.75 to 0.90.

The fact that the abovesaid conditions, selected as indicated, result in hard coating based on maltitol of satisfactory quality was all the more unexpected as, contrary to what occurs in the case of hard coating with saccharose —a disaccharide like maltitol and of behavior close to that of maltitol in numerous other fields—the super-saturation resulting from the said conditions is not high, although it should normally be expected that the super-saturation necessary for obtaining a hard coating of good quality with maltitol is close to that necessary in the case of the disaccharide constituted by saccharose.

It is recalled that, by the expression "saturation level", is denoted the ratio, for a given temperature, of the concentration of the syrup expressed in grams of maltitol per 100 $cm^3$ of water, to the solubility limit of maltitol, at the given temperature, also expressed in grams of maltitol per 100 $cm^3$ of water.

In Table I, are collected for a certain number of temperatures, the values of the solubility limit of the maltitol (expressed in g/100 $cm^3$).

TABLE I

| t °C. | Solubility limit (in g/100 $cm^3$) |
| --- | --- |
| 20 | 153 |
| 25 | 170 |
| 30 | 181 |
| 35 | 193 |
| 40 | 210 |
| 45 | 226 |
| 50 | 241 |

The invention will be still better understood by means of the additional description which follows and the examples which are given with respect to advantageous embodiments.

In order, consequently, to manufacture hard coated products according to the invention, procedure is as follows or in an equivalent manner.

Cores of the confectionery or pharmaceutical product type to be coated, "sugarless" or not, are maintained in the form of a moving bed in a rotating dragee-forming pan of conventional type and equipped with means for controlling the internal temperature.

There is applied, for example by spraying, on said moving core mass a maltitol syrup whose temperature is less than 70° C. and, preferably, from 45° to 65° C.

The maltitol syrup employed has a concentration of dry matter from 50 to 70% by weight, preferably from 55 to 65% by weight.

The richness of this syrup in maltitol is higher than 92%, preferably than 95%, and, more preferably still, than 96% by weight to dry matter.

The temperature existing in the moving core bed is maintained at a temperature below 55° C., preferably from 20° to 40° C.

The concentration in dry matter of the maltitol syrup and the temperature of the core bed within the abovesaid ranges is selected so that, when the maltitol syrup arrives in contact with the cores to be coated, it is at a saturation level from 0.70 to 0.90, preferably from 0.75 to 0.90.

An example of maltitol syrup which has proved satisfying is that of the following composition:
maltitol : 97.1% by weight
sorbitol : 1.1% by weight
maltotriitol : 1.8% by weight.

The coating is carried out by successive cycles each comprising a first phase of addition of the maltitol syrup to the core bed and a second phase during which the addition is stopped while still maintaining the rotation of the pan and the temperature existing within the core mass, the envelope with which the cores have been coated being dried and polished in the course of this phase.

The thickness of the coating is selected as a function particularly of the core to be coated or of the desired effects.

For instance, it is possible to produce a coating of, for example, about 0.5 mm thickness by carrying out successively from 15 to 30 additions, which, taking into account the duration of an addition and the period of time separating the end of one addition from the beginning of the following one results in a total duration of the coating operation of the order of 3 to 7 hours.

The means employed to maintain the temperature within the mass of cores in movement at the desired value, may be constituted by a device for blowing in hot air of controlled temperature.

Due to the coating conditions according to the invention, it is possible to obtain a smooth and regular surface.

The coated products thus obtained have with respect to the coated products obtained by hard coating with a sugarless coating of the prior art, particularly those based on sorbitol, the advantage
—of being of a whiteness very pleasant to see,
—of being of a sweeter taste and
—of being more crunchy.

To optimise the results, it is preferred to apply to the treated cores and before the hard coating proper, a gum layer which may be, for example, based on gum arabic, gelatin or an equivalent substance.

It is possible to add to the maltitol syrup employed, various additives like coloring materials, flavorings or agents improving the surface condition such as beeswax or carnauba wax.

Among the additives, may be mentioned titanium dioxide, along with the flavorings, those of mint, orange and lemon.

In the choice of pharmaceutical products and of confectionery constituting by the core to be coated, recourse is advantageously made, by reason of the fact that the coating applied is "sugarless", to "sugarless" products, particularly based on sorbitol, xylitol, mannitol, maltitol and hydrogenated glucose syrups of the Lycasin ® brand.

When the core to be coated contains a fermentable sugar, the coating obtained according to the invention reduces the cariogenic character of the whole and confers on it in any case the inherent qualities of maltitol.

The hard coated products according to the invention may show a smooth surface essentially free from imperfections and crystalline over the whole thickness of the coating; they are stable, even in atmospheres of high humidity and they show in addition a very pleasant sweet taste.

In the examples which follow, there are contemplated succesively:
—the preparation of a coated chewing-gum according to the invention and, in this respect, the determination of the optimal conditions of hard coating by means of maltitol,
—the preparation of a hard coated confectionery product according to the invention of the "compression product" type,
—the preparation of a hard coated "sugarless" hard candy according to the invention.

EXAMPLE 1

Hard coating with maltitol of a "sugarless" chewing-gum type.

The composition of the plaquettes of chewing-gum used for this example is as follows:

—28 parts by weight of a base gum constituted by that which is marketed by the Dreyfus Company under the name "Extra Paloja",
—20 parts by weight of a hydrogenated glucose syrup (concentrated to 85% of dry matter of DM) constituted by that which is marketed by the Roquette Freres Company under the trademark Lycasin ® 80/55,
—50.8 parts by weight of powdered sorbitol constituted by that which is marketed by the Roquette Freres Company under the trademark Neosorb P60 ®,
—1.2 parts by weight of flavorings and coloring agents. These platelets are prepared by following the operational sequence indicated below:
—after heating to 75° C., the base gum is kneaded in a kneader of the Kustner type provided with a hot water flow, in the presence of the liquid phase constituted by the syrup of hydrogenated glucose; in the course of this step, the solid phase constituted by the powdered sorbitol is added gradually in small amounts; finally the flavorings and coloring agents are added,
—after dusting the paste with mannitol, rolling of the paste and cutting it up into cushions of rectangular shape and of average nominal weight of 0.9 g, is carried out.

500 g of these cushions are placed in laboratory coating pan or dredger of the "LILLIPUT" type marketed by the FROGERAIS Company, equipped with an regulated air blower enabling the temperature of the cushion bed to be maintained constant, and with a thermometric probe positioned in the bed.

The coating pan is driven at a rotary speed comprised between 22 and 25 rpm.

The maltitol based coating syrup is kept at a constant temperature in a thermo-regulated water bath and it is added in successive charges (cycles) of 13 to 30 g of syrup, the introduction being made in some seconds every 3 to 7 minutes. This time, separating the end of one introduction from the following introduction, enables the crystallization of the maltitol and the evaporation of the water to be achieved.

The maltitol syrup used for the coating is essentially constituted of maltitol and has a certain content of sorbitol and maltotriitol.

Before determining by four series of successive experiments the optimal conditions of the method of hard coating with maltitol according to the invention, two comparative experiments are made, consisting of operating respectively under the hard coating conditions with saccharose and with sorbitol.

(a) Comparative experiments

The maltitol syrup used is of a richness of 95% in maltitol, 1.6% in sorbitol and 3.4% in maltotriitol.

The conditions of the first comparative experiment (those of the hard coating with saccharose) and of the second (ythat of the hard coating with sorbitol), as well as the results obtained, are specified in table II.

TABLE II

| No. of the experiment | 1 | 2 |
|---|---|---|
| richness of the syrup | 95% | 95% |
| dry matter of the syrup | 80% | 70% |
| temperature of the moving bed | 30° C. | 30° C. |
| temperature of the syrup | 80° C. | 40° C. |
| number of cycles | 10-15 | 10-15 |
| weight of syrup used | 180 | 180 |

TABLE II-continued

| No. of the experiment | 1 | 2 |
|---|---|---|
| in grams approximately | | |

In both cases, the coated products obtained do not give satisfaction; very pronounced surface defects appeared and are explained by very slow and irregular crystallization, which shows that it is not possible to obtain hard coating with maltitol corresponding to the exigences of practice in simply repeating, what was a priori logical, above all the conditions known beforehand for hard coating with saccharose.

(b) Experiments carried out to determine the optimal conditions of maltitol richness of the syrup used.

By means of four maltitol syrups of different richnesses, there were carried out, under conditions otherwise identical and by means of the previously described equipment, the experiments 3 to 6 whose conditions and results are recorded in table III.

The line reserved for the evaluations enables, by means of the following symbolism, definition of the quality of the hard coating obtained.

| | |
|---|---|
| poor | ooo |
| very mediocre | oo |
| mediocre | o |
| acceptable | x |
| good | xx |
| very good | xxx |

The four maltitol syrups employed are of 60% of dry matter and have a maltitol richness respectively of 92, 95, 96 and 97%.

TABLE III

| No. of the experiment | 3 | 4 | 5 | 6 |
|---|---|---|---|---|
| richness of the syrup | 92% | 95% | 96% | 97% |
| dry matter of the syrup | 60% | 60% | 60% | 60% |
| temperature of the moving bed | 30° C. | 30° C. | 30° C. | 30° C. |
| temperature of the syrup | 50° C. | 50° C. | 50° C. | 50° C. |
| number of cycles | 10–15 | 10–15 | 10–15 | 10–15 |
| weight of syrup used | 250 g | 250 g | 250 g | 250 g |
| saturation level | 0.76 | 0.79 | 0.80 | 0.83 |
| evaluation | oo | o | xx | xxx |

It is observed that with 96 and 97% of richness, the coatings obtained are quite correct, the crystallization of the maltitol is achieved very regularly and requires only a slightly greater drying time in the case of the syrup with 96% richness. The corresponding products show a pleasant crunchiness and sweet taste.

For the syrups with 95 and 92% richness, under these conditions, the chewing-gums have a tendency to stick together, the crystallization is difficult and the drying times are long, these defects being accentuated in the case of the 92% syrup.

(c) Experiments carried out for the determination of the optimal conditions of contenty of dry matter of the syrup used.

A syrup of richness 97% in maltitol was tested for six different contents of dry matter, namely respectively 45, 50, 55, 60, 65 and 70%, which corresponds to experiments 7 to 12.

The conditions and the results of these tests are given in table IV.

TABLE IV

| No. of the experiment | 7 | 8 | 9 | 10 | 11 | 12 |
|---|---|---|---|---|---|---|
| richness of the syrup | 97% | 97% | 97% | 97% | 97% | 97% |
| dry matter of the syrup | 45% | 50% | 55% | 60% | 65% | 70% |
| number of cycles | 10–15 | 10–15 | 10–15 | 10–15 | 10–15 | 10–15 |
| weight of syrup used | 333 g | 300 g | 275 g | 250 g | 230 g | 214 g |
| saturation level | 0.44 | 0.53 | 0.80 | 0.83 | 0.99 | 1.25 |
| evaluation | o | x | xx | xxx | x | oo |

Good results are obtained for contents of dry matter of 50 to 65% and very good results for dry matter of 55 to 60%.

Beyond 65%, the crystallization is irregular and surface defects appear; below 50%, the chewing-gums are sticky and the dry times considerable.

(d) Experiments carried out for the determination of optimal conditions from the point of view of temperature existing in the midst of the bed of moving cores.

A maltitol syrup with 60% dry matter and 97% richness in maltitol is used.

In the six experiments (n°13 to 18) carried out with this syrup, the coating was done at as many different temperatures in the moving bed, the feed syrup being kept at 50° C.

The conditions and the results of these tests are reported in table V.

TABLE V

| No. of the experiment | 13 | 14 | 15 | 16 | 17 | 18 |
|---|---|---|---|---|---|---|
| temperature of the bed | 10° C. | 15° C. | 20° C. | 30° C. | 40° C. | 50° C. |
| number of cycles | 10–15 | 10–15 | 10–15 | 10–15 | 10–15 | 10–15 |
| weight of syrup used | 250 g | 250 g | 250 g | 250 g | 250 g | 250 g |
| saturation level | 1.07 | 1 | 0.95 | 0.81 | 0.69 | 0.60 |
| evaluation | oo | o | x | xxx | xx | o |

It appears on examination of these results that it is advantageous to keep the temperature of the bed between 20° and 40° C.

Under these conditions, the products obtained show good crystallinity of the layer as well as excellent stability on storage.

Due to the softening of the cushions, it was not possible to proceed with any experiment at temperatures higher than 50° C.

(e) Experiments carried out for the determination of optimal conditions from the point of view of the temperature of the syrup.

Six experiments were carried out (19 to 24) using the syrup of experiments 13 to 18, the temperature of the bed having been kept at 30° C.

The other parameters of the test and the results obtained are recorded in table VI.

TABLE VI

| No. of the experiment | 19 | 20 | 21 | 22 | 23 | 24 |
|---|---|---|---|---|---|---|
| temperature of the syrup | 40° C. | 45° C. | 50° C. | 60° C. | 65° C. | 70° C. |
| number of cycles | 10–15 | 10–15 | 10–15 | 10–15 | 10–15 | 10–15 |
| weight of the syrup used | 250 g | 250 g | 250 g | 250 g | 250 g | 250 g |
| saturation level | 0.81 | 0.81 | 0.81 | 0.81 | 0.81 | 0.81 |
| evaluation | o | xx | xxx | xx | o | oo |

In view of these results, it is observed that it is preferable to work under the conditions of the experiment with a maltitol syrup kept at a temperature of 45° to 60° C.

Beyond 60° C., after addition of the syrup, in a first stage, the chewing-gums stick together then a rapid but irregular crystallization occurs; below 40° C., the distribution of the crystalline layer becomes less good and the drying times increase substantially.

On examining all of the rsults obtained in experiments 3 to 24, it appears that, to obtain coating of quality, there is reason to operate at a saturation level of 0.7 to 0.9.

EXAMPLE 2

Hard coating of compression products.

The cores to be coated were prepared by means of a high yield rotary press of type P 1000, marketed by the Wilhelm Fette GmbH Company.

The product used is constituted by sorbitol powder of the brand Neosorb ® 20/60, flavored with mint including 0.3% by weight of a lubricant constituted by magnesium stearate.

The sorbitol tablets thus prepared, of average weight 0.5 g, are round and biconcave.

500 g of these tablets are used.

The coating is conducted by means of the previously used equipment for coating of chewing-gum; each time 10–15 additions are made, spaced by 10 minutes each time, of 15 g of maltitol.

As shown by the results of the 10 experiments (25 to 34) effected with these tablets and recorded in table VII, the coating of these tablets gives good quality products, to the extent that the conditions of saturation level established for the hard coating of chewing-gums, is maintained.

The products obtained show good crystallinity of the layer, good stability in storage and a certain crunchiness in tasting.

The candies were put into the form of spheres of an average diameter of 1.5 cm and average weight 0.9 g.

For the coating, the equipment and the conditions of operation described above are used. The temperature of the bed was in all cases kept at a value below or at least equal to 60° C., this value being imposed by the constituent material of the cores.

The syrup of richness 97% in maltitol is added in 10–15 runs at the rate each time of 13 g every 10 minutes to a quantity of 500 g of candies.

4 experiments are carried out (35 to 38) and the conditions and results shown in table VIII confirm that it is possible possible to hard coat hard candies with maltitol, provided that one operates under conditions of saturation level established in the case of chewing-gums and in that of tablets.

TABLE VIII

| No. of the experiment | 35 | 37 | 38 | 39 |
|---|---|---|---|---|
| dry matter of the syrup | 70% | 60% | 55% | 50% |
| temperature of the bed | 30° C. | 40° C. | 30° C. | 30° C. |
| temperature of the syrup | 50° C. | 50° C. | 50° C. | 50° C. |
| evaluation | o | xx | xxx | x |

I claim:

1. Confectionery or pharmaceutical product provided with a hard sugarless coating obtained by hard coating using a maltitol syrup having a dry matter content from 50 to 70% by weight, the said coating being essentially crystalline and comprising at least 90% by weight of maltitol.

2. Method of providing a confectionery or pharmaceutical product with a sugarless hard coating obtained by hard coating, wherein a maltitol syrup
   —having a richness in maltitol higher than 92% with respect to the dry matter,
   —having a dry matter content from 50 to 70% by weight
   —having a temperature less than 70° C., is applied on a moving bed of cores to be coated, the temperature existing in said moving core bed being less than 55° C., all of the abovesaid conditions being selected, within the above-mentioned ranges, so that, when the maltitol syrup arrives in contact with the cores to be coated, that is to say at the temperature existing within the moving core bed, it is at a saturation level of 0.70 to 0.90.

3. Method according to claim 2, wherein the richness in maltitol with respect to dry matter is higher than 96%.

4. Method according to claim 2, wherein the dry

TABLE VII

| No. of the experiment | 25 | 26 | 27 | 28 | 29 | 30 | 31 | 32 | 33 | 34 |
|---|---|---|---|---|---|---|---|---|---|---|
| richness of the syrup | 97% | 97% | 97% | 96% | 97% | 97% | 97% | 92% | 97% | 97% |
| dry matter of the syrup | 45% | 60% | 55% | 60% | 60% | 50% | 45% | 60% | 60% | 60% |
| temperature of the bed | 30° C. | 30° C. | 30° C. | 30° C. | 40° C. | 30° C. | 30° C. | 30° C. | 50° C. | 60° C. |
| saturation level | 0.44 | 0.83 | 0.8 | 0.8 | 0.69 | 0.53 | 0.44 | 0.76 | 0.60 | 0.48 |
| evaluation | o | xxx | xxx | xx | xx | x | o | oo | o | ooo |

EXAMPLE 3

Hard coating of "sugarless" type hard candies.

Hard candies were prepared by evaporating to a residual moisture content of 0.5%, a hydrogenated starch hydrolysate, marketed under the brand Lycasin ® 80/55.

matter content of the maltitol syrup is from 55 to 65% by weight.

5. Method according to claim 2, wherein the temperature of the maltitol syrup is from 45° to 65° C.

6. Method according to claim 2, wherein the temperature existing in the moving bed of cores is from 20° to 40° C.

7. Method according to claim 2, wherein the saturation level of the maltitol syrup is from 0.75 to 0.90.

8. Method of providing a confectionery or pharmaceutical product with a sugarless hard coating obtained by hard coating, wherein a maltitol syrup
— having a richness in maltitol higher than 96% with respect to the dry matter,
— having a dry matter content from 55 to 65% by weight and
— having a temperature from 45° to 65° C., is applied on a moving bed of cores to be coated, the temperature existing in said moving core bed being from 20° to 40° C., all of the abovesaid conditions being selected, within the above-mentioned ranges, so that, when the maltitol syrup arrives in contact with the cores to be coated, that is to say at the temperature existing within the moving core bed, it is at a saturation level of 0.75 to 0.90.

* * * * *